United States Patent [19]
Madison et al.

[11] Patent Number: 5,370,826
[45] Date of Patent: Dec. 6, 1994

[54] QUATERNAY OXAZIRIDINIUM SALTS AS BLEACHING COMPOUNDS

[75] Inventors: Stephen A. Madison, New City, N.Y.; Janet L. Coope, Cliffside Park, N.J.

[73] Assignee: Lever Brothers Company, Division of Conopco, Inc., New York, N.Y.

[21] Appl. No.: 151,483

[22] Filed: Nov. 12, 1993

[51] Int. Cl.$^5$ .................. C11D 3/28; C11D 3/395; D06L 1/12; D06L 3/02
[52] U.S. Cl. .................. 252/102; 8/111; 134/2; 134/25.2; 252/99; 252/186.42; 252/186.43; 252/186.44; 252/524; 252/542
[58] Field of Search .............. 8/111; 252/99, 102, 252/186.42, 186.43, 186.44, 524, 542; 546/89, 150; 134/2, 25.2

[56] References Cited

U.S. PATENT DOCUMENTS

| | | | |
|---|---|---|---|
| 3,796,715 | 3/1974 | Leimgruber | 546/150 |
| 4,194,987 | 3/1980 | Brubaker | 252/102 |
| 4,678,792 | 7/1987 | Nickl | 514/307 |
| 5,041,232 | 8/1991 | Batal et al. | |
| 5,045,223 | 9/1991 | Batal et al. | |
| 5,047,163 | 9/1991 | Batal et al. | |
| 5,286,401 | 2/1994 | Dung | 252/102 |

OTHER PUBLICATIONS

Hanquet, Lusinchi & Milliet, Tetrahedron vol. 49, No. 2, pp. 423–428, (Jan. 1993).
Hanquet, Lusinchi, Tet. Let. vol. 34, No. 33, pp. 5299–5302 (Aug. 1993).
Hanquet, Lusinchi & Milliet, Tet. Let. vol. 29, No. 32, pp. 3941–3944 (Aug. 1988).
Hanquet, Lusinchi & Milliet, Tet. Let. No. 29, No. 23, pp. 2817–2818, (May, 1988).
Hanquet, Lusinchi & Milliet, C. R. Acad. Sci. Paris, pp. 625–628, (1991).

*Primary Examiner*—Dennis Albrecht
*Attorney, Agent, or Firm*—Milton L. Honig

[57] ABSTRACT

Novel bleach catalysts, a method for bleaching substrates using these catalysts and detergent compositions containing same are reported. The bleaches are of the quaternary oxaziridinium salt type. Substrates such as fabrics may be bleached in an aqueous solution containing the quaternary oxaziridinium salt.

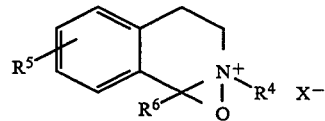

wherein:

$R^4$ may be a substituted or unsubstituted radical selected from the group consisting of hydrogen, aryl, heterocyclic ring, alkyl and cycloalkyl radicals;

$R^5$ and $R^6$ may be a substituted or unsubstituted radical selected from the group consisting of hydrogen, aryl, heterocyclic ring, alkyl, cycloalkyl, nitro, halo, cyano, alkoxy, keto, carboxylic and carboalkoxy radicals; and $X^-$ is a counterion stable in the presence of oxidizing agents.

22 Claims, No Drawings

QUATERNAY OXAZIRIDINIUM SALTS AS BLEACHING COMPOUNDS

BACKGROUND OF THE INVENTION

1. Field of the Invention

The invention relates to a new type of low temperature bleaching system and a method of cleaning substrates therewith.

2. The Related Art

Many household and personal care products are formulated with an active oxygen-releasing material to effect removal of stain and soil. Oxygen-releasing materials have an important limitation; their activity is extremely temperature dependent. Temperatures in excess of 60° C. are normally required to achieve any bleach effectiveness in an aqueous wash system. Especially for cleaning fabrics, high temperature operation is both economically and practically disadvantageous.

The art has partially solved the aforementioned problem through the use of activators. These activators, also known as bleach precursors, often appear in the form of carboxylic acid esters. In an aqueous liquor, anions of hydrogen peroxide react with the ester to generate the corresponding peroxyacid which oxidizes the stained substrate. Commercial application of this technology is found in certain fabric bleaching detergent powders incorporating tetraacetylethylenediamine (TAED) and sodium nonanoyloxybenzene sulfonate (SNOBS).

TAED is effective only under warm-hot wash conditions, i.e. above 30° C. Although this material is widely employed in Europe with laundry detergent, cold water consumer washing habits have not permitted use in the United States. SNOBS can operate at lower temperatures than TAED. For this reason, it has been commercialized in the United States but its performance could still be improved.

Another problem with carboxylic acid ester precursors such as TAED and SNOBS is that conversion to peracid is inefficient. A further difficulty is that they are not catalytic. Once the ester has been perhydrolyzed, it can no longer be recycled.

Accordingly, relatively large amounts of precursor are necessary. Amounts as high as 8% may be necessary in a detergent formulation for bleaching fabrics. At such high use levels, cost for these relatively expensive chemicals is of major concern.

Recently there has been reported In U.S. Pat. No. 5,045,233 by Batal and Madison, a novel bleach based upon N-sulfonyloxaziridines. While these compounds have been shown to be highly effective, even better catalysts are sought, especially for wash temperatures around 10° C., such as are experienced in Japan.

Outside the context of consumer products, there have been reports of novel oxidizing agents. Hanquet and coworkers, in a series of articles, reported preparation of a new class of stable olefin epoxidizing agents, namely oxaziridinium salts. See Hanquet, Lusinchi and Milliet, Tet, Let. (1988) 3941; Hanquet, Lusinchi and Milliet, C. R. Acad. Sci. Paris (1991) Series II, 625; and Hanquet, Lusinchi and Milliet, Tet, Let. (1988) 2817. These oxaziridinium salts were prepared by peracid or monopersulfate oxidation of a corresponding quaternary imine salt under alkaline conditions. Epoxides were reported to be formed from the reaction of olefins with the oxaziridinium salts. Reactions were conducted either In organic solvents or in organic solvent-water biphasic media. Beyond use as a synthetic tool, there is no suggestion of any possible application for oxaziridinium salt chemistry to the problem of removing stains in consumer applications, such as in cleaning fabrics.

It is an object of the present Invention to provide an improved bleaching system and detergent composition containing such system that operates over a wide temperature range including that of under 30° C.

A further object of the present invention is to provide bleach improvement through catalysts effective in relatively small amounts so as to avoid any substantial incremental costs.

A still further object of the present invention is to provide a method for bleaching stained substrates such as clothes, household hard surfaces including sinks, toilets and the like, and even dentures.

Other objects of the present invention will become more readily apparent through the following summary, detailed description and examples.

SUMMARY OF THE INVENTION

A bleaching composition is provided comprising:
(i) from about 1 to about 60% by weight of a peroxygen compound;
(ii) from about 0.01 to about 10% of an oxygen transfer agent whose structure is:

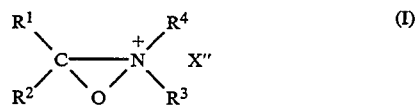

wherein:
- $R^1$ and $R^4$ may be a substituted or unsubstituted radical selected from the group consisting of hydrogen, phenyl, aryl, heterocyclic ring, alkyl and cycloalkyl radicals:
- $R^2$ may be a substituted or unsubstituted radical selected from the group consisting of hydrogen, phenyl, aryl, heterocyclic ring, alkyl, cycloalkyl, nitro, halo, cyano, alkoxy, keto, carboxylic and carboalkoxy radicals;
- $R^3$ may be a substituted or unsubstituted radical selected from the group consisting of phenyl, aryl, heterocyclic ring, alkyl, cycloalkyl, nitro, halo, and cyano radicals;
- $R^1$ with $R^2$ and $R^2$ with $R^3$ may respectively together form a radical selected from the group consisting of cycloalkyl, polycyclo, heterocyclic and aromatic ring systems; and
- $X^-$ is a counterion stable in the presence of oxidizing agents.

Additionally, there Is provided a method for bleaching a stained substrate comprising treating the step of applying to the stained substrate an aqueous solution comprising a peroxygen compound and an oxygen transfer agent whose structure is

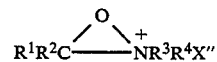

with radical groups as defined above, the mole ratio of peroxygen compound to oxygen transfer agent being from about 250:1 to about 1:2.

DETAILED DESCRIPTION

It has been found that certain types of quaternary oxaziridinium salts can operate as catalysts on peroxygen compounds to transfer active oxygen to stains. Consumer and industrial articles can effectively be bleached to remove stains present on such articles. Thus, quaternary oxaziridinium salt chemistry is more than a synthetic curiosity as in the conversion of olefins to epoxides reported by Hanquet et al. Unlike the Hanquet et al reaction medium that requires an organic solvent, quaternary oxaziridinium salts can be devised for use in completely aqueous wash systems.

Quaternary oxaziridinium salts covered by the present invention are those whose structure is:

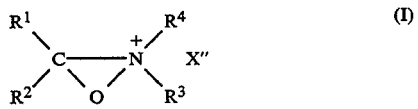

wherein:

$R^1$ and $R^4$ may be hydrogen or a $C_1$–$C_{30}$ substituted or unsubstituted radical selected from the group consisting of phenyl, aryl, heterocyclic ring, alkyl and cycloalkyl radicals;

$R^2$ may be hydrogen or a $C_1$–$C_{30}$ substituted or unsubstituted radical selected from the group consisting of phenyl, aryl, heterocyclic ring, alkyl, cycloalkyl, nitro, halo, cyano, alkoxy, keto, carboxylic and carboalkoxy radicals;

$R^3$ may be a $C_1$–$C_{30}$ substituted or unsubstituted radical selected from the group consisting of phenyl, aryl, heterocyclic ring, alkyl, cycloalkyl, nitro, halo, and cyano radicals;

$R^1$ with $R^2$ and $R^2$ with $R^3$ may respectively together form a radical selected from the group consisting of cycloalkyl, polycyclo, heterocyclic or aromatic ring systems.

$X^-$ is a counterion stable in the presence of oxidizing agents.

Heterocyclic rings according to this invention include cycloaliphatic and cycloaromatic type radicals incorporating an oxygen, sulfur and/or nitrogen atom within the ring system. Representative nitrogen heterocycles include pyridine, pyrrole, imidazole, triazole, tetrazole, morpholine, pyrrolidine, piperidine and piperazine. Suitable oxygen heterocycles include furan, tetrahydrofuran and dioxane. Sulfur heterocycles may include thiophene and tetrahydrothiophene.

Counterion $X^-$ may be selected from chloride, bromide, sulfate, methosulfate, sulfonate, p-toluenesulfonate, borontetrafluoride, $PF_5^-$, phosphate and cyano radicals.

The term "substituted" is defined in relation to $R^1$, $R^2$, $R^3$ and $R^4$ as a substituent which is a nitro, halo, cyano, $C_1$–$C_{20}$ alkyl, amino, aminoalkyl, thioalkyl, sulfoalkyl, carboxyester, hydroxy, $C_1$–$C_{20}$ alkoxy, polyalkoxy or $C_1$–$C_{40}$ quaternary di- or tri-alkylammonium function.

The most preferred quaternary oxaziridine salt is the 3,4-dihydroisoquinolinium salts of structure II where $R^5$ and $R^6$ are defined by the same radicals as that for $R^2$:

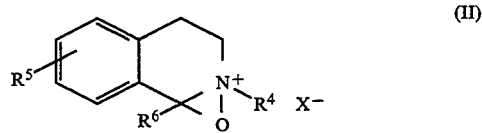

Table I lists specific Illustrative compounds represented by structure II.

TABLE I

| COMPOUND | $R^4$ | $R^5$ | $R^6$ | $X^-$ |
|---|---|---|---|---|
| 1 | $CH_3$ | H | H | $BF_4^-$ |
| 2 | $CH_3$ | H | H | p-tosylate$^-$ |
| 3 | $CH_3$ | $CH_3$ | H | $Cl^-$ |
| 4 | $CH_3$ | $NO_2$ | H | $Br^-$ |
| 5 | $CH_3$ | Cl | H | $BF_4^-$ |
| 6 | $CH_3$ | $OCH_3$ | H | brosylate$^-$ |
| 7 | phenyl | H | H | $CH_3SO_4^-$ |
| 8 | benzyl | phenyl | H | $Cl^-$ |
| 9 | $(CH_2)_2OH$ | CN | H | $PF_6^-$ |
| 10 | $CH_3$ | $CH_2COCH_3$ | H | $PF_6^-$ |
| 11 | $(CH_3)_2CH$ | $COCH_3$ | H | $CH_2CH_3SO_4^-$ |
| 12 | $CH_3$ | $SO_2^-Na^+$ | N | $Cl^-$ |
| 13 | $CH_3(CH_2)_{11}$ | H | H | p-tosylate$^-$ |
| 14 | $CH_3(CH_2)_{15}$ | Br | H | $CH_3SO_4^-$ |
| 15 | $CH_2CH_2N(CH_2)_3$ | H | H | $Cl^-$ |
| 16 | $CH_3$ | F | H | $Cl^-$ |
| 17 | $CH_3$ | $CF_3$ | H | $PF_6^-$ |
| 18 | $CH_3$ | $CH_2OPO_3Na_2$ | H | $Cl^-$ |
| 19 | $CH_3$ | pyridyl | H | $Cl^-$ |
| 20 | 2-pyridyl | H | H | $Cl^-$ |
| 21 | $CH_3$ | $CH_2N^+(CH_3)_3$ | H | $CH_3SO_4^-$ |
| 22 | $CH_3CH_2O(CH_2)_2$ | H | H | $CH_3SO_4^-$ |
| 23 | $CH_3$ | $(CH_2)_7CH_3$ | H | $Cl^-$ |
| 24 | $CH_3$ | $CO_2^-Na^+$ | H | $Cl^-$ |
| 25 | $(CH_2)_7CH_3$ | H | H | p-tosylate |
| 26 | $CH_3$ | H | $CH_3$ | Cr |
| 27 | $CH_3$ | H | phenyl | Cr |

Additional compounds according to the present Invention are outlined below as structures III through X.

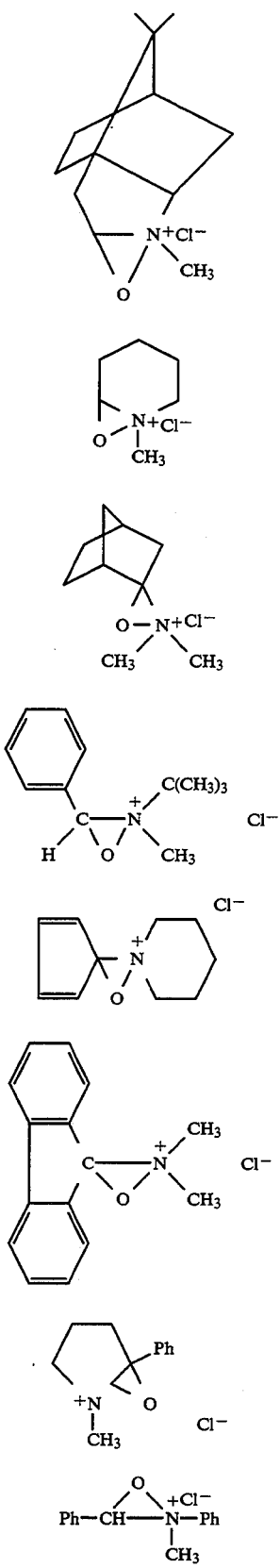

The foregoing oxygen transfer agents may be incorporated into detergent bleach compositions along with a further essential component which is a peroxygen compound capable of yielding peroxide anion in an aqueous solution.

Amounts of oxygen transfer agent suitable for the present invention may range from about 0.01 to 10%, preferably from about 0.2 to 5%, optimally from about 0.5 to 1.5% by weight of the composition.

The peroxygen compound may be present from about 1 to 60%, preferably from about 1.5 to 25%, optimally from about 2 to 10% by weight.

The molar ratio of peroxide anion (or a peroxygen compound generating the equivalent amount of peroxide anion) to oxygen transfer agent will range from about 1500:1 to about 1:2, preferably from about 150:1 to 1:1, optimally from about 60:1 to 3:1.

Peroxide anion sources are well-known in the art. They include the alkalimetal peroxides, organic peroxides such as urea peroxide, and inorganic persalts, such as the alkalimetal perborates, percarbonates, perphosphates, persilicates and persulfates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions.

Alkylhydroperoxides are another suitable class of peroxygen compounds. Examples of these materials Include cumene hydroperoxide and t-butyl hydroperoxide.

Organic peroxyacids may also be suitable as the peroxygen compound. Such materials have a general formula:

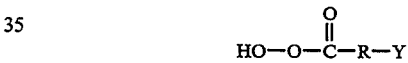

wherein R is an alkylene or substituted alkylene group containing from 1 to about 22 carbon atoms or a phenylene or substituted phenylene group, and Y is hydrogen, halogen, alkyl, aryl or

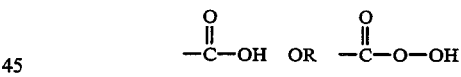

The organic peroxyacids usable in the present invention can contain either one or two peroxy groups and can be either aliphatic or aromatic.

When the organic peroxyacid is aliphatic, the unsubstituted acid has the general formula:

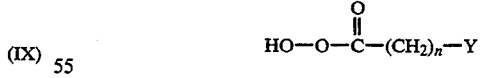

where Y can be, for example, H, $CH_3$, $CH_2Cl$, COOH, or COOOH; and n is an integer from 1 to 20.

When the organic peroxy acid Is aromatic, the unsubstituted acid has the general formula:

wherein Y is hydrogen, alkyl, haloalkyl, halogen or COOH or COOOH.

Typical monoperoxyacids useful herein include alkyl peroxyacids and aryl peroxyacids such as:

(i) peroxybenzoic acid and ring-substituted peroxybenzoic acid, e.g. peroxy-α-naphthoic acid;

(ii) aliphatic, substituted alliphatic and arylalkyl monoperoxy acids, e.g. peroxylauric acid, peroxystearic acid, and N,N-phthaloylaminoperoxycaproic acid (PAP); and (iii) amidoperoxyacids, e.g. mononoylamide of either peroxysuccinic acid (NAPSA) or of peroxyadipic acid (NAPAA).

Typical diperoxyacids useful herein include alkyl diperoxyacids and aryldiperoxy acids, such as:

(iii) 1,12-diperoxydodecanedioic acid;

(iv) 1,9-diperoxyazelaic acid;

(v) diperoxybrassylic acid; diperoxysebacic acid and diperoxyisophthalic acid;

(vi) 2-decyldiperoxybutane-1,4-dioic acid;

(vii) 4,4'-sulfonylbisperoxybenzoic acid; and (viii) N,N'-terephthaloyl-di(6-aminoperoxycaproic acid) (TPCAP).

Particularly preferred organic acids are peracetic acid, monoperoxyphthalic acid (magnesium salt hexahydrate), PAP, TPCAP and diperoxydodecanedioic acid. Under certain circumstances, hydrogen peroxide itself may directly be employed as the peroxygen compound.

Bleach systems of the present Invention may be employed for a wide variety of purposes, but are especially useful in the cleaning of laundry. When intended for such purpose, the peroxygen compound and oxygen transfer agent of the present invention will usually also be combined with surface-active materials, detergency builders and other known ingredients of laundry detergent formulations.

The surface-active material may be naturally derived, such as soap or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from about 1% to about 40% by weight of the composition, most preferably 4 to 25%.

Synthetic anionic surface-actives are usually water-soluble alkali metal salts of organic sulfates and sulfonates having alkyl radicals containing from about 8 to about 22 carbon atoms.

Examples of suitable synthetic anionic detergent compounds are sodium and ammonium alkyl sulfates, especially those obtained by sulfating higher ($C_8$–$C_{18}$) alcohols produced for example from tallow or coconut oil; sodium and ammonium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow or coconut oil and synthetic alcohols derived from petroleum; sodium coconut oil fatty acid monoglyceride sulfates and sulfonates; sodium and ammonium salts of sulfuric acid esters of higher ($C_9$–$C_{18}$) fatty alcohol-alkylene oxide, particularly ethylene oxide reaction products; the reaction products of fatty acids such as coconut fatty acids esterified with isethionic acid and neutralized with sodium hydroxide; sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolyzing with a base to produce a random sulfonate; sodium and ammonium $C_7$–$C_{12}$ dialkyl sulfosuccinates; and olefinic sulfonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulfonates; sodium ($C_{16}$–$C_{18}$) alkyl sulfates and sodium ($C_{16}$–$C_{18}$)alkyl ether sulfates.

Examples of suitable nonionic surface-active compounds which may be used preferably together with the anionic surface-active compounds, include in particular, the reaction products of alkylene oxides, usually ethylene oxide, with alkyl ($C_6$–$C_{22}$) phenols, generally 2–25 ene oxide, i.e. 2–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylenediamine. Other so-called nonionic surface-actives include alkyl polyglycosides, polyhydroxy fatty acid amides (e.g. $C_{12}$–$C_{18}$ N-methyl glucamide), long chain tertiary amine oxides, long chain tertiary phosphine oxides and dialkyl sulfoxides.

Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

Soaps may also be Incorporated Into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between about 0.5 and about 25% by weight, with lower amounts of about 0.5 to about 5% being generally sufficient for lather control. Amounts of soap between about 2 and about 20%, especially between about 5 and about 15%, are used to give a beneficial effect on detergency. This is particularly valuable in compositions used in hard water when the soap acts as a supplementary builder.

The detergent compositions of the invention will normally also contain a detergency builder. Builder materials may be selected from (1) calcium sequestrant materials; (2) precipitating materials; (3) calcium ion-exchange materials; and (4) mixtures thereof.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, tartrate mono- and di-succinates, oxydisuccinate, crystalline or amorphous aluminosilicates and mixtures thereof.

Polycarboxylic homo- and copolymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from 1 to 80% by weight, preferably from 10 to 60% by weight.

Upon dispersal In a wash water, the initial amount of peroxygen compound should range in amount to yield anywhere from about 0.05 to about 250 ppm active oxygen per liter of water, preferably between about 1 to 50 ppm. Within the wash media the amount of oxygen transfer agent initially present should be from about 0.01 to about 300 ppm, preferably from about 1 to 100 ppm. Surfactant should be present In the wash water from about 0.05 to 1.0 grams per liter, preferably from 0.15 to 0.40 grams per liter. When present, the builder amount will range from about 0.1 to 3.0 grams per liter.

Apart from the components already mentioned, the detergent compositions of the invention can contain any of the conventional additives in the amounts in which such materials are normally employed in detergent compositions. Examples of these additives Include lather boosters such as alkanolamides, particularly the monoethanolamides derived from palmkernel fatty acids and coconut fatty acids, lather depressants such as alkyl phosphates and silicones, antiredeposition agents such as sodium carboxymethylcellulose and alkyl or substituted alkylcellulose ethers, other stabilizers such as ethylenediaminetetraacetic acid, fabric softening agents, inorganic salts such as sodium sulfate and usually present in very small amounts, fluorescent whitening agents, perfumes, enzymes such as proteases, cellulases, lipases and amylases, germicides and colorants.

Stained consumer products benefiting from treatment with compositions of this invention may include clothes and other fabrics; household fixtures and applicances such as sinks, toilet bowls and oven ranges; tableware such as drinking glasses, dishes, cookware and utensils; and even dentures. Hair colorants may also be formulated with the bleach composition of this invention. The bleaching system of this invention may also be applied to industrial uses such as for the bleaching of wood pulp.

The system of the present invention may be delivered in a variety of product forms including powders, on sheets or other substrates, in pouches, in tablets, In aqueous liquids, or in nonaqueous liquids such as liquid nonionic detergents.

The following examples will more fully illustrate the embodiments of this invention. All parts, percentages and proportions referred to herein and in the appended claims are by weight unless otherwise illustrated.

EXAMPLE 1

Preparation of N-Methyl-1,2-Oxo-1,2,3,4-Tetrahydroisoquinolinium Tetrafluoroborate The preparation of title compound was performed in a two-step process as described in Hanquet et al, *Tetrahedron*, 49, 423 (1993).

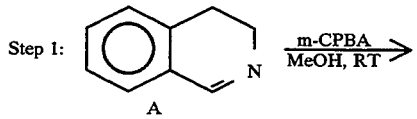

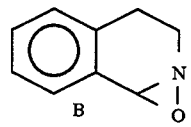

Step 2: B + (CH$_3$)$_3$OBF$_4$ $\xrightarrow{CH_2Cl_2}$

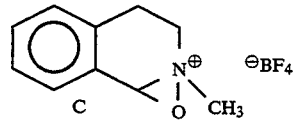

Step 1: Preparation of Oxaziridine (Compound B)

3,4-Dihydroisoquinoline (compound A, 1.03 g, 7.863 mmol) was dissolved in 14 ml MeOH at RT in a small round-bottomed flask rifled with a condenser and drying tube. While stirring, 85% m-chloroperbenzoic acid (1.59 g, 7.863 mmol active oxygen) was added all at once (no heat observed) and the resulting reaction mixture stirred at RT for 1.0 hour. All solids were observed to go into solution. The clear MeOH solution was diluted with an equal volume of water and extracted with 20 ml CH$_2$Cl$_2$. The CH$_2$Cl$_2$ extract was then washed three times with 25 ml of 7.5% NaHCO$_3$, once with 25 ml water and the CH$_2$Cl$_2$ extract was dried over MgSO$_4$. Removal of CH$_2$Cl$_2$ yielded 0.94 g crude brown colored liquid product. Iodometric titrations gave typically 72 to 75% activity. IR (neat) showed the characteristic oxazirane ring absorbances at 1260 and 1275 and 750 (br) cm$^{-1}$. $^1$H NMR (CD$_3$CN, 200 MHz) δ 7.10–8.10 (4H, m), 4.95 (1H,s,C1), 3.90 (1H,m,C3), 2.90 (2H,m,C4) 2.55 (1H,m,C3).

Step 2: Preparation of Oxaziridinium-BF$_4$ (Compound C)

Trimethyloxonium tetrafluoroborate (0.95 g, 6.395 retool) dried in a desiccator under high vacuum prior to use, was weighed out under N$_2$ in a dry box and suspended with stirring in 2.0 ml anhydrous CH$_2$Cl$_2$ in a small round bottom flask fitted with condenser and N$_2$ flush system, and cooled using crushed dry ice. To this was added compound B prepared above (0.94 g, 6.395 mmol based on 100% purity) dissolved in 2.0 ml anhydrous CH$_2$Cl$_2$. The dry ice was then replaced by an ice bath/NaCl, and the reaction mixture was stirred under cooling to 0° C. for about 1.5 hours, during which time solids formed. The flask was stoppered tightly and stored in the freezer overnight. The reaction mixture was then allowed to warm up in an ice bath and the solids then filtered, washed with a small amount of CH$_2$Cl$_2$ and dried in a vacuum desiccator. Yield of colorless solids was 0.84 g. Iodometric titration showed 87.34% activity: m.p. 85°–102° C. (lit. 99°–101° C.). $^1$H NMR (CD$_3$CN, 300 MHz) δ 7.83 (1H, d, J=7.5 Hz, C6), 7.65 (1H, d of t, J=1.4, 7.6 Hz, C8), 7.51 (1H, t, J=7.5 Hz, C7), 7.39 (1H, d, J=7.9 Hz, C9), 6.15 (1H, s, C1), 4.33 (1H, ddd, J=13.4, 6.2, 2.0 Hz, Ha), 3.88 (ddd, J=13.4, 12.3, 5.0 Hz, Hb), 3.31 (3H, s, N-CH3), 3.21–2.86 (2H, m, Hc and Hd). $^{13}$C NMR was in agreement with literature values.

The proton NMR assignments in the literature for compounds B (Ogata et al, *J. Amer. Chem. Soc,* (1973), 4692) and C (Hanquet) do not include the resonance at 3.9 and 3.88, respectively. COSY experiments on C show strong coupling between the protons at 4.33, 3.88 and 3.21–2.86 ppm; therefore, these protons must be part of the same molecule. Additionally, compound B decomposes to isoquinoline upon storage in the refrigerator after 1–2 weeks with proportional loss of the resonances at 3.9, 2.9 and 2.55 ppm.

EXAMPLE 2

Stain bleaching experiments were conducted In a Terg-O-Tometer in 500 mL of milli-Q water using two tea-stained cotton cloths measuring 3×4 inches. In a typical test, 0.75 g of Surf® added to the system and the pH of the solution was constantly buffered to the indicated level by the addition of dilute aqueous sodium hydroxide or hydrochloric acid. The oxaziridinium salt was then added to the system. Washes were carried out at the indicated temperature for 15 minutes.

Stain bleaching was measured reflectometrically using a Colorgard System/05 Reflectometer. ΔR is the reflectance difference between washed and unwashed cloths. Bleaching was indicated by an increase in reflectance, reported as ΔΔR. In general a ΔΔR of one unit is perceivable in a paired comparison while ΔΔR of two units is perceivable monadically.

Table I and II report the bleaching performance of the oxaziridinium salt of N-methyl-3,4-dihydroisoquinoline (denoted Oxaz Quat).

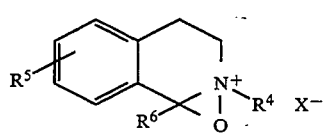

wherein:
R$^4$ may be a substituted or unsubstituted radical selected from the group consisting of hydrogen, aryl, heterocyclic ring, alkyl, cycloalkyl, nitro, halo, cyano, alkoxy, keto, carboxylic and carboalkoxy radicals; and X$^-$ is a counterion stable in the presence of oxidizing agents.

3. A composition according to claim 1 wherein the peroxygen compound is present in an amount from about 1.5 to 25% and the oxygen transfer agent is present in an amount from about 0.2 to 5% by weight.

4. A composition according to claim 1 wherein the peroxygen compound is an inorganic material selected from the group consisting of perborate, percarbonate, perphosphate, persilicate and monopersulphate salts.

5. A composition according to claim 1 wherein the peroxygen compound is an organic peroxyacid.

6. A composition according to claim 5 wherein the organic peroxyacid is selected form the group consist-

TABLE II

Bleaching of Tea Stained (BC-1) Cloths with Oxaz Quat
pH 9.5, 1.02 g/l Ultra Surf ®, 15 minute wash

| TEMPERATURE (°C.) | ppm a.o. | CONCENTRATION | ΔR ULTRA SURF ® | ΔR SURF ® + OXAZ QUAT | ΔΔR OXAZ QUAT |
|---|---|---|---|---|---|
| 11 | 7.5 | 4.69 × 10$^{-4}$M | −1.7 | 16.6 | 18.3 |
| 11 | 4.0 | 2.48 × 10$^{-4}$M | −2.4 | 12.3 | 14.7 |
| 32 | 7.5 | 4.69 × 10$^{-4}$M | −0.6 | 15.8 | 16.4 |
| 42 | 7.5 | 4.69 × 10$^{-4}$M | −0.1 | 10.9 | 11.0 |

TABLE III

Bleaching of Wine Stained (EMPA-114) Cloths with Oxaz Quat
pH 9.5, 1.02 g/l Ultra Surf ®, 15 minute wash

| TEMPERATURE (°C.) | ppm a.o. | CONCENTRATION | ΔR ULTRA SURF ® | ΔR SURF ® + OXAZ QUAT | ΔΔR OXAZ QUAT |
|---|---|---|---|---|---|
| 11 | 7.5 | 4.69 × 10$^{-4}$M | 8.9 | 14.3 | 5.4 |
| 32 | 7.5 | 4.69 × 10$^{-4}$M | 13.1 | 16.4 | 3.3 |

Based on the results in Tables II and III, it is evident that the oxaziridinium quat salt has a pronounced effect upon improving bleaching of both tea and wine stained cloths. At lower temperatures, the oxidant surprisingly performs better than at higher wash temperatures.

The foregoing description and Examples illustrate selected embodiments of the present invention. In light thereof, various modifications will be suggested to one skilled in the art, all of which are within the spirit and purview of this invention.

What is claimed is:

1. A bleaching composition comprising:
   (i) from about 1 to about 60% by weight of a peroxygen compound;
   (ii) from about 0.01 to about 10% by weight of an oxygen transfer agent which is an oxaziridinium compound derived from a 3,4-dihydroisoquinolinium salt; and
   (iii) from about 0.5 to about 50% of a surfactant.

2. A composition according to claim 1 wherein the oxaziridinium compound is defined by the structure:

ing of peracetic acid, monoperoxyphthalic acid, diperoxydodecanedioic acid, N,N'-terephthaloyl-di(6-aminoperoxycaproic acid) and N,N'-phthaloylaminoperoxycaproic acid.

7. A composition according to claim 5 wherein the organic peroxyacid is an amidoperoxyacid.

8. A composition according to claim 1 further comprising a bleach precursor present in an amount such that the molar ratio of bleach precursor relative to oxygen transfer agent ranges from about 250:1 to about 1:20.

9. A composition according to claim 1 further comprising from about 1 to 80% of a detergent builder.

10. A composition according to claim 1 further comprising an effective amount for cleaning of an enzyme selected from the group consisting of proteases, cellulases, lipases, amylases and mixtures thereof.

11. A composition according to claim 1 delivered in a form selected from the group consisting of a powder, sheet, pouch, tablet, aqueous liquid and nonaqueous liquid.

12. A composition according to claim 2 wherein said substituent on, $R^4$, $R^5$ and $R^6$ is a functional unit selected from the group consisting of nitro, halo, cyano, $C_1$–$C_{20}$ alkyl, amino, aminoalkyl, thioalkyl, sulfoxyalkyl, carboxyester, hydroxy, $C_1$–$C_{20}$ alkoxy, polyalkoxy, $C_1$–$C_{40}$ quaternary di- or tri-alkylammonium functional units and mixtures thereof.

13. A method for bleaching a stained substrate, said method comprising contacting said stained substrate in an aqueous medium with an oxygen transfer agent which is an oxaziridinium compound derived from a 3,4-dihydroisoquinolinium salt.

14. A method according to claim 13 wherein the oxaziridinium compound has the structure:

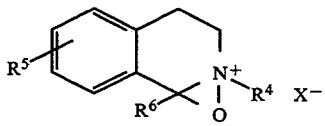

wherein:
$R^4$ may be a substituted or unsubstituted radical selected from the group consisting of hydrogen, aryl, heterocyclic ring, alkyl and cycloalkyl radicals;

$R^5$ and $R^6$ may be a substituted or unsubstituted radical selected from the group consisting of hydrogen, aryl, heterocyclic ring, alkyl, cycloalkyl, nitro, halo, cyano, alkoxy, keto, carboxylic and carboalkoxy radicals; and $X^-$ is a counterion stable in the presence of oxidizing agents.

15. A method according to claim 13 wherein the aqueous medium further comprises a peroxygen compound and the molar ratio of peroxygen compound to oxygen transfer agent ranges from about 1500:1 to 1:20.

16. A method according to claim 15 wherein the aqueous medium further comprises a bleach precursor and the molar ratio of the bleach precursor to oxygen transfer agent ranges from about 250:1 to 1:20.

17. A method for bleaching a stained substrate, said method comprising contacting said stained in an aqueous medium with a surfactant and an oxygen transfer agent which is an oxaziridinium compound derived from a 3,4-dihydroisoquinolinium salt, said surfactant and oxygen transfer agent being present in said aqueous medium in an amount from about 0.05 to 1.0 grams per liter and from about 0.01 to about 300 ppm, respectively, per liter of medium.

18. A method according to claim 17 wherein the oxaziridinium compound has the structure:

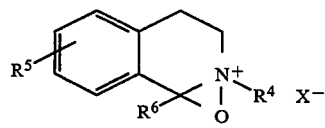

wherein:
$R^4$ may be a substituted or unsubstituted radical selected from the group consisting of hydrogen, aryl, heterocyclic ring, alkyl and cycloalkyl radicals;

$R^5$ and $R^6$ may be a substituted or unsubstituted radical selected from the group consisting of hydrogen, aryl, heterocyclic ring, alkyl, cycloalkyl, nitro, halo, cyano, alkoxy, keto, carboxylic and carboalkoxy radicals; and $X^-$ is a counterion stable in the presence of oxidizing agents.

19. A method according to claim 17 wherein said medium comprises surfactant in an amount from about 0.15 to about 0.40 grams per liter and oxygen transfer agent in an amount of from about 5 to about 100 ppm per liter of medium.

20. A method according to claim 17 wherein the molar ratio of peroxygen compound to oxygen transfer agent ranges from about 1500:1 to about 1:1 and the molar ratio of bleach precursor to oxygen transfer agent ranges from about 100:1 to about 1:1.

21. A method according to claim 17 wherein said substrate is selected from the group consisting of fabrics, household fixtures and tableware.

22. A method according to claim 17 wherein said substrate is a denture.

* * * * *